US011033594B2

(12) United States Patent
Potnis et al.

(10) Patent No.: US 11,033,594 B2
(45) Date of Patent: *Jun. 15, 2021

(54) ORAL GEL FOR SENSITIVITY AND TOOTH PAIN

(71) Applicant: Colgate-Palmolive Company, New York, NY (US)

(72) Inventors: Shashank Potnis, Thane (IN); Ravi Subramanyam, Mumbai (IN); Rajitha Nair, Mumbai (IN)

(73) Assignee: Colgate-Palmolive Company, New York, NY (US)

( * ) Notice: Subject to any disclaimer, the term of this patent is extended or adjusted under 35 U.S.C. 154(b) by 391 days.

This patent is subject to a terminal disclaimer.

(21) Appl. No.: 14/648,715

(22) PCT Filed: Mar. 7, 2013

(86) PCT No.: PCT/IN2013/000135
§ 371 (c)(1),
(2) Date: Jun. 1, 2015

(87) PCT Pub. No.: WO2014/087419
PCT Pub. Date: Jun. 12, 2014

(65) Prior Publication Data
US 2016/0143978 A1  May 26, 2016

(30) Foreign Application Priority Data

Dec. 6, 2012 (IN) ............... 3759/DEL/2012

(51) Int. Cl.
| *A61K 36/61* | (2006.01) |
| *A61K 9/00* | (2006.01) |
| *A61K 31/125* | (2006.01) |
| *A61K 47/18* | (2017.01) |
| *A61K 47/32* | (2006.01) |
| *A61K 31/085* | (2006.01) |
| *A61K 9/06* | (2006.01) |
| *A61K 31/045* | (2006.01) |
| *A61K 36/48* | (2006.01) |
| *A61K 36/185* | (2006.01) |

(52) U.S. Cl.
CPC ............ *A61K 36/61* (2013.01); *A61K 9/0053* (2013.01); *A61K 9/06* (2013.01); *A61K 31/045* (2013.01); *A61K 31/085* (2013.01); *A61K 31/125* (2013.01); *A61K 47/183* (2013.01); *A61K 47/32* (2013.01); *A61K 36/185* (2013.01); *A61K 36/48* (2013.01)

(58) Field of Classification Search
CPC ................. A61K 36/61; A61K 31/125
See application file for complete search history.

(56) References Cited

U.S. PATENT DOCUMENTS

| 3,925,543 A | 12/1975 | Donohue |
| 3,932,605 A | 1/1976 | Vit |
| 3,932,608 A | 1/1976 | Anderson et al. |
| 3,943,241 A | 3/1976 | Anderson et al. |
| 3,988,434 A | 10/1976 | Schole et al. |
| 4,011,309 A | 3/1977 | Lutz |
| 4,022,880 A | 5/1977 | Vinson et al. |
| 4,025,616 A | 5/1977 | Haefele |
| 4,042,680 A | 8/1977 | Muhler et al. |
| 4,064,138 A | 12/1977 | Saari et al. |
| 4,100,269 A | 7/1978 | Pader |
| 4,108,979 A | 8/1978 | Muhler et al. |
| 4,108,981 A | 8/1978 | Muhler et al. |
| 4,146,607 A | 3/1979 | Ritchey |
| 4,154,813 A | 5/1979 | Kleinberg |
| 4,160,821 A | 7/1979 | Sipos |
| 4,213,961 A | 7/1980 | Curtis et al. |
| 4,225,579 A | 9/1980 | Kleinberg |
| 4,259,316 A | 3/1981 | Nakashima et al. |
| 4,269,822 A | 5/1981 | Pellico et al. |
| 4,305,928 A | 12/1981 | Harvey |
| 4,335,102 A | 6/1982 | Nakashima et al. |
| 4,339,432 A | 7/1982 | Ritchey et al. |
| RE31,181 E | 3/1983 | Kleinberg |
| 4,466,954 A | 8/1984 | Ichikawa et al. |
| 4,528,181 A | 7/1985 | Morton et al. |
| 4,532,124 A | 7/1985 | Pearce |
| 4,538,990 A | 9/1985 | Pashley |
| 4,645,662 A | 2/1987 | Nakashima et al. |

(Continued)

FOREIGN PATENT DOCUMENTS

| WO | WO 09/100277 | 8/2009 |
| WO | WO 14/087420 | 6/2014 |

OTHER PUBLICATIONS

Chatterjee et al., 2005, "Bacterial Acidification and CaviStat Alkalinization of Occlusal Fissure pH," Abstract, 83rd Session of the American Association for Dental Research, Mar. 9-12, 2005, Baltimore, MD.

Cummins, 2010, "Recent advances in dentin hypersensitivity: Clinically proven treatments for instant and lasting sensitivity relief," American Journal of Dentistry 23(Spec. Iss. A):3A-13A.

Fu et al., 2010, "Instant dentin hypersensitivity relief of a new desensitizing dentifrice containing 8.0% arginine, a high cleaning calcium carbonate system and 1450 ppm fluoride: A 3-day clinical study in Chengdu, China," American Journal of Dentistry 23(Spec. Iss. A):20A-27A.

(Continued)

Primary Examiner — Amy L Clark

(57) ABSTRACT

Disclosed herein are orally acceptable topical analgesic gels comprising a mixture of analgesic oils comprising (a) clove oil and/or eugenol, (b) a cooling agent, and (c) camphor, in an orally acceptable gel base, the gel base comprising an anionic polymer and a basic amino acid, and the analgesic gel providing controlled release of the mixture of analgesic oils following application to a tooth together with a methods of making and using the same.

22 Claims, No Drawings

(56) References Cited

U.S. PATENT DOCUMENTS

| | | | |
|---|---|---|---|
| 4,656,031 A | 4/1987 | Lane et al. | |
| 4,725,576 A | 2/1988 | Pollock et al. | |
| 4,997,640 A | 3/1991 | Bird et al. | |
| 5,096,700 A | 3/1992 | Seibel et al. | |
| 5,286,480 A | 2/1994 | Boggs et al. | |
| 5,334,617 A | 8/1994 | Ulrich et al. | |
| 5,370,865 A | 12/1994 | Yamagishi et al. | |
| 5,639,795 A | 6/1997 | Friedman et al. | |
| 5,747,004 A | 5/1998 | Giani et al. | |
| 5,762,911 A | 6/1998 | Kleinberg et al. | |
| 5,906,811 A | 5/1999 | Hersh | |
| 5,922,332 A | 7/1999 | Fossel | |
| 5,922,346 A | 7/1999 | Hersh | |
| 5,997,301 A | 12/1999 | Linden | |
| 6,217,851 B1 | 4/2001 | Kleinberg et al. | |
| 6,319,513 B1* | 11/2001 | Dobrozsi | A61K 9/0043 424/434 |
| 6,436,370 B1 | 8/2002 | Kleinberg et al. | |
| 6,488,961 B1 | 12/2002 | Robinson et al. | |
| 6,524,558 B2 | 2/2003 | Kleinberg et al. | |
| 6,531,115 B1 | 3/2003 | Singh et al. | |
| 6,558,654 B2 | 5/2003 | McLaughlin | |
| 6,805,883 B2 | 10/2004 | Chevaus et al. | |
| 2002/0081360 A1 | 6/2002 | Burgard et al. | |
| 2004/0147605 A1* | 7/2004 | Onuki | A61K 9/0095 514/561 |
| 2005/0175959 A1 | 8/2005 | Jodaikin et al. | |
| 2006/0140882 A1* | 6/2006 | Tambs | A61K 8/22 424/53 |
| 2008/0267891 A1 | 10/2008 | Zaidel et al. | |
| 2010/0135921 A1* | 6/2010 | Hughes | A61K 8/25 424/49 |
| 2010/0322873 A1 | 12/2010 | Kohli et al. | |

OTHER PUBLICATIONS

International Search Report and Written Opinion in International Application No. PCT/IN2013/000135, dated Nov. 7, 2013.

Kleinberg, 1999. "A New Saliva-Based Anticaries Composition," Dentistry Today 18(2):1-6.

Kleinberg, 2002, "A Mixed-Bacteria Ecological Approach to Understanding the Role of the Oral Bacteria in Dental Caries Causation: An Alternative to *Streptococcus mutans* and the Specific-Plaque Hypothesis," Critical Reviews in Oral Biological Medicine 13(2):108-125.

Lavender et al., 2010, "Mode of action studies on a new desensitizing dentifrice containing 8.0% arginine, a high cleaning calcium carbonate system and 1450 ppm fluoride," American Journal of Dentistry 23(Spec. Iss. A):14A-19A.

Leffingwell, 2009, "Cooling Ingredients and Their Mechanisms of Action", Chapter 65, from Barel, et al. (Eds), Handbook of Cosmetic Science and Technology, 3rd ed. Informa Healthcare.

Machado et al., 2007, "CaviStat confetion inhibition of Caries in Posterior Teeth," Abstract, 83rd Session of the American Association for Dental Research, Mar. 21-24, 2007, New Orleans, LA.

Packaging with Ingredient List for DenClude® (launched Dec. 2004).

Packaging with Ingredient List for ProClude® (launched Jul. 2002).

Que et al., 2010, "Dentin hypersensitivity reduction of a new toothpaste containing 8.0% arginine and 1450 ppm fluoride: An 8-week clinical study on Chinese adults," American J of Dentistry 23(Spec. Iss. A):28A-35A.

Yin et al., 2010, "Extrinsic stain removal efficacy of a new desensitizing dentifrice containing 8.0% arginine, calcium carbonate and 1450 ppm fluoride," American J. of Dentistry 23(Spec. Iss. A):36A-40A.

* cited by examiner

ORAL GEL FOR SENSITIVITY AND TOOTH PAIN

BACKGROUND

Tooth pain is most often caused by structural damage to the tooth, wherein the nerves of the tooth, which are normally well protected by dentin and enamel, is exposed to external stimuli, for example as a result of caries, a cracked tooth, an exposed tooth root, or erosion of the enamel, as well as by gum disease, abscess, or impaction. The severity of a toothache can range from chronic and mild to sharp and excruciating. The pain may be aggravated by chewing or by cold or heat. The patient may not be able to identify the cause of the pain without a dental examination. Current symptomatic treatments include pharmaceutical analgesics—non-steroidal anti-inflammatory agents such as such as aspirin, ibuprofen, or acetaminophen, topical gel anesthetics containing lidocaine or benzocaine, and/or narcotics such as codeine—but these pharmaceuticals each have their own limitations, in that they may not be available without a prescription, may not have an immediate effect, and/or may have undesirable side effects. Home remedies may provide a brief respite from the pain, but do not remain for extended periods on the tooth and typically do not provide controlled delivery of the active ingredient or sustained pain relief.

There is a need for improved methods of treating tooth pain, which address the various types of pain, for example pain from cavities as well as from dental hypersensitivity, and which provide immediate and sustained relief from the pain.

SUMMARY

The invention provides, in a first aspect, a novel topical "leave on" gel formulation that permits sustained delivery of pain-relieving herbal extracts to the affected tooth.

The orally acceptable analgesic "leave-on" gel formulation of the invention comprises a mixture of analgesic oils comprising (a) clove oil and/or eugenol, (b) a cooling agent, e.g., selected from menthol, peppermint oil, menthyl esters, menthoxyalkanols, and p-menthane carboxamides (e.g., N-ethyl-p-menthane-3-carboxamide), and mixtures thereof; and (c) camphor, in an orally acceptable gel base, the gel base comprising an anionic polymer and a basic amino acid such as arginine, the formulation providing a sustained release of the mixture of analgesic oils following application. In one embodiment, the gel base comprises
  a. poly(acrylic acid), e.g., carbomer homopolymer type B, e.g., Carbopol® 974P NF;
  b. methyl vinyl ether/maleic anhydride (PVM/MA) copolymer;
  c. propylene glycol;
  d. nonionic surfactant selected from poloxamers, polysorbates, and mixtures thereof;
  e. basic amino acid, e.g. arginine, e.g. in an amount sufficient to neutralize the anionic polymer(s);
  f. water; and
  g. optionally sweeteners, flavorings, and/or preservatives.

In other aspects, the invention provides methods of making such formulations and of using such formulations to alleviate tooth pain. It has surprisingly been discovered that these oils are more effective as analgesics in combination with one another, perhaps because they affect different receptors. Formulation presents some challenges, as the oral cavity is essentially an aqueous environment, and the analgesic oils are only poorly soluble in water, but the structured formulations provided give stable formulations as well as effective and sustained release of the analgesic oils upon application.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used herein, the term "effective amount" means the quantity of analgesic oils required to provide an anti-sensitivity or pain relieving effect. Tooth pain may be a result of caries, a cracked tooth, an exposed tooth root, or erosion of the enamel, as well as by gum disease, abscess, or impaction.

In some embodiments, the present invention provides in a first embodiment, an orally acceptable topical analgesic gel (Formulation 1) comprising an orally acceptable topical analgesic gel comprising a mixture of analgesic oils comprising (a) clove oil and/or eugenol, (b) a cooling agent, and (c) camphor, in an orally acceptable gel base, the gel base comprising an anionic polymer and a basic amino acid, the formulation providing a sustained release of the mixture of analgesic oils following application to a tooth.

For example, the invention provides e.g., 1.1. Formulation 1 wherein the gel base provides sustained release of the analgesic herbal oils for a period of at least three, e.g. at least five minutes, e.g. at least 10 minutes, e.g., at least 20 minutes following application of the formulation to a tooth.

1.2. Formulation 1 or 1.1 wherein the mixture of analgesic oils comprises 1-10% by weight of the formulation, e.g., about 5%.

1.3. Any of the preceding formulations wherein the ratio of (a) to (b) to (c) is 70-100:5-15:5-15, e.g., about 8:1:1 to about 10:1:1.

1.4. Any of the preceding formulations wherein the mixture of analgesic oils comprises eugenol or clove oil:menthol:camphor in a ratio of 70-100:5-15:5-15, e.g., about 8:1:1 to about 10:1:1.

1.5. Any of the preceding formulations wherein the cooling agent is a TRMP8 thermoreceptor agonist, e.g., selected from peppermint oil, menthol, menthoxyalkanols (e.g., 3-(1-menthoxy)-2-methylpropane-1,2-diol, 3-(1-menthoxy)ethanol, 3-(1-menthoxy)propan-1-ol, and 3-(1-menthoxy)butan-1-ol), menthyl esters (e.g., menthyl lactate and menthyl 3-hydroxybutarate), and p-menthane 3-carboxamides (e.g., N-ethyl-p-menthane-3-carboxamide (WS-3), (1R,2S,5R)-N-(4-methoxyphenyl)-p-menthanecarboxamide (WS-12), (2S,5R)-N-[4-(2-Amino-2-oxoethyl)phenyl]-p-menthane-carboxamide, N-cyclopropyl-5-methyl-2-isopropylcyclohexanecarbonecarboxamide, ethyl 3-(p-menthane-3-carboxamido)acetate (WS-5), (1R,2S,5R)-N-(4-Methoxyphenyl)-p-menthanecarboxamide (WS-12), N-ethyl-2,2-diisopropylbutanamide (WS-27), N-cyclopropyl-5-methyl-2-isopropylcyclohexanecarboxamide, N-(1,1-Dimethyl-2-hydroxyethyl)-2,2-diethylbutanamide (WS-116), N-(4-cyanomethylphenyl)-p-menthanecarboxamide, and N-(2-

(pyridin-2-yl)ethyl)-3-p-menthanecarboxamide; for example N-ethyl-p-menthane-3-carboxamide), and mixtures thereof.

1.6. Any of the preceding formulations wherein the cooling agent is menthol.

1.7. Any of the preceding formulations wherein the basic amino acid is selected from arginine, lysine, citrullene, ornithine, creatine, histidine, diaminobutanoic acid, diaminoproprionic acid.

1.8. Any of the preceding formulations wherein the basic amino acid is arginine.

1.9. Any of the preceding formulations wherein the basic amino acid is present in an amount sufficient to partially or fully neutralize the anionic polymer, e.g., from 4-12%, e.g. about 8%.

1.10. Any of the preceding formulations wherein the anionic polymer is a polycarboxylate, e.g., selected from poly(acrylic acid)(optionally cross-linked, e.g., with polyalkenyl ethers or divinyl glycol) and optionally additionally comprising 1:4 to 4:1 copolymers of maleic anhydride or acid with another polymerizable ethylenically unsaturated monomer (e.g., methyl vinyl ether/maleic anhydride (PVM/MA) copolymer), in free or salt form.

1.11. Any of the preceding formulations wherein the gel base comprises one or more nonionic surfactants, e.g., selected from poloxamers, polysorbates, and mixtures thereof.

1.12. Any of the preceding formulations wherein the gel base has pH 6-8, e.g., wherein the gel base is approximately pH neutral.

1.13. Any of the preceding formulations wherein the gel base further comprises one or more astringents, e.g., herbal astringents, e.g. selected from *Terminalia arjuna* and *Acacia* extracts or powders.

1.14. Any of the preceding formulations wherein the gel base further comprises a soluble potassium salt, e.g., potassium nitrate.

1.15. Any of the preceding formulations wherein the gel base further comprises a small particle occlusive agent, e.g. a small particle silica or calcium carbonate, having a $d_{50}$ of less than 5 µm, e.g., 0.5-5 µm, e.g. a small particle synthetic amorphous silica (e.g. $d_{50}$ about 3-4 µm) and/or small particle precipitated calcium carbonate (e.g., $d_{50}$ about 0.5-3 µm).

1.16. Any of the preceding formulations wherein the mixture of analgesic oils further comprises comprising a warming agent, e.g., a TRPV1 thermoreceptor agonists, e.g., black pepper oil, ginger oil, vanilla extract, vanillyl butyl ether, capsicum tincture, or mixtures of any of these, e.g., ginger oil, pepper oil or mixtures thereof.

1.17. Any of the preceding formulations wherein the mixture of analgesic oils further comprises an anti-inflammatory herbal oil, e.g., a phenolic herbal oil, for example thymol.

1.18. Any of the preceding formulations wherein the gel base comprises sweeteners, e.g. saccharin, flavorings (in addition to the analgesic oils), and/or preservatives, e.g., sodium benzoate.

1.19. Any of the preceding formulations wherein the gel base comprises:
 a. cross-linked poly(acrylic acid), e.g., carbomer homopolymer type B, e.g., Carbopol® 974P NF;
 b. propylene glycol;
 c. nonionic surfactant selected from poloxamers, polysorbates, and mixtures thereof;
 d. neutralizing base, e.g., sodium hydroxide; and
 e. water.

For example, in one aspect the invention provides Formulation 1.17, an orally acceptable topical analgesic gel according to any of the preceding formulations comprising

| | |
|---|---|
| Carbomer homopolymer type B | 1-2%, e.g. about 1.5% |
| Methyl vinyl ether/maleic anhydride copolymer | 1-3%, e.g. about 2% |
| L-Arginine | 6-10%, e.g. about 8% |
| Propylene Glycol | 10-20%, e.g., about 15% |
| Poloxamer | 5-15%, e.g., about 9% |
| Polysorbate | 2-7%, e.g., about 5% |
| Sodium Saccharin | 0-0.5%, e.g., about 0.2% |
| Sodium Benzoate | 0-0.5%, e.g., about 0.2% |
| Base, e.g., NaOH | To adjust to pH 6-8 |
| Clove oil or eugenol | 3-6%, e.g., about 4-5% |
| Camphor | 0.2-0.8%, e.g., about 0.5% |
| Menthol | 0.2-0.8%, e.g., about 0.5% |
| Water | 30-75% |

In other aspects, the invention provides methods of making such formulations and of using such formulations to alleviate tooth pain.

For example, the invention provides a method of alleviating dental pain comprising administering an effective amount of a composition of any of Formulation 1, et seq. to the affected area, e.g., wherein the composition is left on the affected area following application, e.g. for at least a minute, e.g., at least 5 minutes. The invention further provides any of Formulation 1, et seq. for use in alleviating dental pain.

In another embodiment, the invention provides the use of a mixture of analgesic oils comprising (a) clove oil and/or eugenol, (b) a cooling agent (e.g., as hereinbefore described, e.g., selected from menthol, peppermint oil, menthyl esters, menthoxyalkanols, and p-menthane carboxamides (e.g., N-ethyl-p-menthane-3-carboxamide), and mixtures thereof); and (c) camphor, together with an anionic polymer and a basic amino acid, in the manufacture of an orally acceptable topical analgesic gel, e.g., a gel according to any of Formulation 1, et seq., to alleviate dental pain.

In another embodiment, the invention provides a method of making an orally acceptable topical analgesic gel, e.g., as hereinbefore described, e.g., any of Formulation 1, et seq. the orally acceptable topical analgesic gel comprising a mixture of analgesic oils comprising (a) clove oil and/or eugenol, (b) a cooling agent, and (c) camphor; together with an orally acceptable gel base comprising a cross-linked poly(acrylic acid) polymer, nonionic surfactants, a basic amino acid, and water, the method comprising first forming a water-in-oil emulsion wherein the oil phase comprises the mixture of analgesic oils, the water phase comprises the poly(acrylic acid) polymer and water, and the nonionic surfactants facilitate the emulsion formation, then adding the basic amino acid to raise the pH of the emulsion thus formed to a level sufficient to ionize the carboxyl groups on the cross-linked poly(acrylic acid) polymer, thereby forming a stable gel.

Analgesic oils: In various embodiments, the invention provides compositions comprising a mixture of analgesic oils comprising (a) clove oil and/or eugenol; (b) a cooling agent, e.g., selected from peppermint oil, menthol, menthyl esters, menthoxyalkanols, and p-menthane 3-carboxamides), and mixtures thereof; and (c) camphor. These analgesic oils may be from natural sources or may be synthetic. Clove oil is extracted from the buds, leaf or stem of the clove plant, *Syzygium aromaticum*. Where clove oil is used in place of eugenol, the amount used may be adjusted, so that the amount of eugenol (typically 80-90% of the clove oil) is constant. Camphor may be extracted from plants, e.g., from laurel or rosemary, or synthetically produced, e.g., from oil of turpentine. Cooling agents are known in the art and are described, e.g., in Leffingwell, "Cooling Ingredients and Their Mechanisms of Action", Chapter 65, from Barel, et al. (Eds), *Handbook of Cosmetic Science and Technology*, 3$^{rd}$ ed. Informa Healthcare (2009), the contents of which are incorporated herein by reference. Cooling agents include natural or synthetic TRMP8 thermoreceptor agonists, for example, menthol, which is the dominant component of peppermint oil, and its various derivatives, e.g., compounds having a p-menthane (1-methyl-4-isopropyl-cyclohexyl) moiety, for example menthyl esters, menthoxyalkanols, and p-menthane 3-carboxamides. The analgesic oils may in some embodiments additionally comprise one or more warming agents, e.g., TRPV1 thermoreceptor agonists, e.g., black pepper oil, ginger oil, vanilla extract, vanillyl butyl ether, capsicum tincture, or mixtures thereof, for example in an amount of 0.1-2%, e.g., ca. 0.5% ginger oil and 0.5% black pepper oil. The analgesic oils may in some embodiments additionally comprise one or more anti-inflammatory herbal oils, e.g., selected from the phenolic herbal oil, for example thymol, for example in an amount of 0.1-2%, e.g., ca. 0.5% thymol.

The gels of the invention in various embodiments utilize anionic polymers, which tend to stick to the soft and hard surfaces of the oral cavity, and provide targeted sustained delivery of the analgesic oils. Carbomers or polyacrylates, for example the various Carbopol® products, are cross-linked poly(acrylic acid) polymers, and may in certain embodiments form the principal structurant for the gels. For example, the gel may comprise cross-linked poly(acrylic acid), e.g., carbomer homopolymer type B, for example Carbopol® 974P NF. These polymers have low viscosity at low pH, permitting mixing of the various components of the gel, and formation of an emulsion or suspension of the analgesic oils, but when the pH is raised by addition of a basic material, the carboxyl moieties ionize and repel one another, causing the polymer to swell and the viscosity to increase. The oil droplets trapped in the matrix remain stably suspended in the formulation, and are then released upon application. Thus the polyacrylate component is typically added in the form of the free acid and then partially or fully neutralized with a suitable base in the final formulation to form water soluble alkali metal (e.g., potassium and sodium) or ammonium salts. The polyacrylate is provided in an amount sufficient to provide a viscous gel in the final formulation, e.g., 0.5-3%, for example 1-1.5%. The compositions of the invention may in some embodiments comprise additional polymers, for example 1:4 to 4:1 copolymers of maleic anhydride or acid with another polymerizable ethylenically unsaturated monomer (e.g., methyl vinyl ether/maleic anhydride (PVM/MA) copolymer), e.g., having a molecular weight (M.W.) of about 30,000 to about 1,000,000, most preferably about 300,000 to about 800,000. Methyl vinyl ether/maleic anhydride (PVM/MA) copolymers include the Gantrez® product line. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805.

The additional anionic polymers when present may be present m amounts ranging from about 0.05 to about 3% by weight. Finally, in some embodiments, the compositions comprise additional thickening agents, for example, polyvinyl pyrrolidone (PVP, e.g. Plasdone® S-630), and/or silica thickeners, which form polymeric structures or gels in aqueous media, may be present. Note that these silica thickeners are physically and functionally distinct from particulate silica abrasives often used in dentifrice formulations, as the silica thickeners are very finely divided and provide little or no abrasive action. Other thickening agents may include carboxyvinyl polymers, carrageenan, hydroxyethyl cellulose and/or water soluble salts of cellulose ethers such as sodium carboxymethyl cellulose and sodium carboxymethyl hydroxyethyl cellulose. Natural gums such as karaya, gum arable, and gum tragacanth may also be incorporated. Colloidal magnesium aluminum silicate can also be used as component of the thickening composition to further improve the composition's texture. In certain embodiments, thickening agents in addition to the polycarboxylate may be found in an amount of about 0.5% to about 10.0% by weight of the total composition are used.

Basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater, and can thus be used to at least partially neutralize the acidic anionic polymers of the formulations. Accordingly, basic amino acids include, but are not limited to, arginine, lysine, citrullene, ornithine, creatine, histidine, diaminobutanoic acid, diaminoproprionic acid, salts thereof or combinations thereof. In a particular embodiment, the basic amino acids are selected from arginine, citrullene, and ornithine. In certain embodiments, the basic amino acid is arginine, for example, l-arginine, or a salt thereof. The amount of basic amino acid depends on the particular formulation and in some embodiments will simply be the amount necessary to provide a pH of 6-8, e.g. approximately neutral pH to the formulation. In various embodiments, the basic amino acid will be present in amounts of 4-12% w/w of the formulation, e.g., about 8%.

In some embodiments, the invention comprises a small particle occlusive agent, capable of plugging the dentinal tubules and reducing sensitivity of the teeth. The small particle occlusive agent may, for example, be a small particle silica or calcium carbonate, having a $d_{50}$ of less than 5 pm, e.g., 0.5-5 μm, e.g. small particle synthetic amorphous silica ($d_{50}$ about 3-4 μm) and/or small particle precipitated calcium carbonate ($d_{50}$ about 0.5-3 μm). For example, commercially available Sorbosil AC43 silica has a $d_{50}$ of 3.95 μm. The $d_{50}$ is measured using particle size measuring techniques as known in the art. For example, particle size distribution may be measured using a Malvern Particle Size Analyzer, Model Mastersizer 2000 (or comparable model) (Malvern Instruments, Inc., Southborough, Mass.), wherein a helium-neon gas laser beam is projected through a transparent cell which contains silica, such as, for example, silica hydrogel particles suspended in an aqueous solution. Light rays which strike the particles are scattered through angles which are inversely proportional to the particle size. The photodetector arrant measures the quantity of light at several predetermined angles. Electrical signals proportional to the measured light flux values are then processed by a microcomputer system, against a scatter pattern predicted from theoretical particles as defined by the refractive indices of the sample and aqueous dispersant to determine the particle size distribution of the silica hydrogel, for example. It will be understood that other methods of measuring particle size are known in the art, and based on the disclosure set forth herein, the skilled artisan will understand how to calculate median particle size, mean particle size, and/or particle size distribution of particles in the present invention.

In certain embodiments, the emulsion of the oil in the gels of the invention is facilitated by surfactants. In some embodiments, the surfactants are nonionic surfactants. Illustrative nonionic surfactants that can be used in the compositions of the invention include compounds produced by the condensation of alkylene oxide groups (generally hydrophilic) with an organic hydrophobic compound which may be aliphatic or alkylaromatic. Examples of nonionic surfactants include, but are not limited to, the poloxamers (e.g., nonionic triblock copolymers composed of a central hydrophobic chain of polyoxypropylene (polypropylene oxide)) flanked by two hydrophilic chains of polyoxyethylene (polyethylene oxide)), for example commercially available under the trade names Pluronic® or Kolliphor®, e.g., poloxamer 407), polysorbates (polyethoxylated sorbitan esterified with fatty acids, for example commercially available as Alkest®, Canarcel® or Tween®, e.g. polysorbate 20) and mixtures thereof. Other nonionic surfactants which may be used include polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. The surfactant or mixtures of compatible surfactants can be present in the compositions of the present invention in an amount sufficient to permit formation of an oil-in water emulsion between (i) the water and other hydrophilic components of the gel and (ii) the analgesic oils, e.g., in about 0.1% to about 20.0%, for example about 5% to about 20% by weight of the total composition.

In some embodiments, the viscosity of the compositions of the invention is greater than about 1,000 centipoise (cPs) and less than about 900,000 cPs, in a more specific embodiment greater than about 10,000 cP and less than about 100,000 cPs, in a more specific embodiment greater than 50,000 cPs and less than 900,000 cPs, and in an even more specific embodiment from between about 200,000 cPs to about 600,000 cPs.

The compositions of the invention may optionally comprise other components, for example humectants, e.g., propylene glycol and/or glycerin, flavoring agents (in addition to the analgesic oils), sweetening agents, e.g. sodium saccharin, preservatives, e.g. sodium benzoate, basifying agents, e.g. sodium hydroxide, and/or coloring agents.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Embodiments of the present invention are further described in the following examples. The examples are merely illustrative and do not in any way limit the scope of the invention as described and claimed.

EXAMPLES

Example 1

Gels are prepared with the following ingredients:

TABLE 1

1% Oil

| Ingredient | % w/w |
|---|---|
| Carbomer (Carbopol 974P NF) | 1 |
| Propylene glycol | 30 |
| 18% w/v NaOH solution | 1 |
| Sodium saccharin | 0.2 |
| Poloxamer 407 | 10 |
| Oil blend (clove oil:menthol:camphor 50:20:30) | 1 |
| Water | q.s. |

TABLE 2

2% Oil

| Ingredient | % w/w |
|---|---|
| Carbomer (Carbopol 974P NF) | 1 |
| Propylene glycol | 40 |
| 18% w/v NaOH solution | 1 |
| Sodium saccharin | 0.2 |
| Poloxamer 407 | 4 |
| Polysorbate 20 | 2 |
| Oil blend (clove oil:menthol:camphor 50:30:20) | 2 |
| Water | q.s. |

TABLE 3

3% Oil

| Ingredient | % w/w |
|---|---|
| Carbomer (Carbopol 974P NF) | 1 |
| Propylene glycol | 15 |
| 18% w/v NaOH solution | 0.5 |
| Sodium saccharin | 0.2 |
| Poloxamer 407 | 9 |
| Polysorbate 20 | 3 |
| Sodium benzoate | 0.2 |
| Oil blend (clove oil:menthol:camphor 50:20:30) | 3 |
| Water | q.s. |

TABLE 4

5% Oil

| Ingredient | % w/w |
|---|---|
| Carbomer (Carbopol 974P NF) | 1 |
| Propylene glycol | 15 |
| 18% w/v NaOH solution | 0.5 |
| Sodium saccharin | 0.2 |
| Poloxamer 407 | 9 |
| Polysorbate 20 | 3 |
| Sodium benzoate | 0.2 |
| Oil blend (clove oil:menthol:camphor 50:20:30) | 5 |
| Water | q.s. |

Briefly, the carbomer is dispersed in propylene glycol and water and stirred; then surfactant(s), sweetener, and preservative are premixed, added and stirred. Then the oil blend is added, and the mixture homogenized. Finally the alkali is added, which raises the pH of the mixture and causes the carboxylate groups on the carbomer to ionize, resulting in a thick gel. The above formulations with varying amounts of oil component are prepared, the properties of the formulation observed, and the formulation applied to the tooth and gum of a volunteer:

TABLE 5

OPTIMIZATION OF OIL BLEND CONCENTRATION

| Formulation prototype | Comments |
| --- | --- |
| 1.0% Carbopol 974P NF gel with 1% oil blend | Consistency of gel is like an ointment. Warm-cool sensation observed, but with little numbing |
| 1.0% Carbopol 974P NF gel and 2% oil blend | Consistency of gel thinner, warm-cool sensation observed but with little numbing, sweetness good, some oil separation |
| 1.0% Carbopol 974P NF gel and 3% oil blend | Thick, translucent gel, good spreadability, evenness, good sweetness, warm-cool sensation, fair numbing |
| 1.0% Carbopol 974P NF gel and 5% oil blend | Thick translucent gel, good spreadability, evenness, sweetness less, instant numbing, burning sensation, noticeable cool sensation of menthol. |

While none of the formulations are completely unacceptable, the 5% blend appears stable, despite the higher oil level, and provides good delivery of effective levels of active agent.

Optimization of the oil blend composition: The 5% oil formulation described above is then varied using different oil blend compositions as follows:

TABLE 6

OPTIMIZATION OF OIL BLEND COMPOSITION

| Formulation | Comments |
| --- | --- |
| 1.0% Carbopol 974P NF gel and 5% Clove oil:Menthol:Camphor (50:20:30) | Thick translucent gel, good spreadability, evenness, instant numbing, burning sensation, noticeable cool sensation of menthol. |
| 1.0% Carbopol 974P NF gel and 5% Eugenol:Peppermint:Camphor (50:20:30) | Thick translucent gel, good spreadability, evenness, sweetness less, slow numbing with less burning sensation, coolness not noticeable, bitterness observed |
| 1.0% Carbopol 974P NF gel and 5% Eugenol:N-ethyl-p-menthane-3-carboxamide:Camphor (50:20:30) | Thick translucent gel, good spreadability, evenness, sweetness less, slow numbing with less burning sensation, coolness instant but not long lasting, not as good as menthol |
| 1.0% Carbopol 974P NF gel and 5% Eugenol:Menthol:Camphor (70:10:20) | Gel thickness good, appearance translucent and appealing. Good numbing with pleasant warm cool sensation, bitterness less. |
| 1.0% Carbopol 974P NF gel and 5% Eugenol:Menthol:Camphor (80:10:10) | Good gel properties, considered best overall, submitted for further evaluation. |

A larger quantity of the final formulation is prepared, along with a placebo formulation comprising 0.5% methanol, but no clove oil or camphor, as well as an additional formulation with clove oil in place of eugenol (amount of clove oil adjusted to provide an equivalent amount of eugenol), as set forth in Table 7 (below). These formulations are tested in subjects, and the formulations of Option 1 and 1A are found to have good application and retention properties as well as providing excellent relief of dental pain in comparison with the placebo formulation.

TABLE 7

| | Formula option | | |
| --- | --- | --- | --- |
| | PLACEBO | OPTION-1 | OPTION-1A |
| | | Description | |
| | Placebo with 0.5% Menthol | 5% oil blend (Eugenol:Menthol:Camphor, 80:10:10) | 5.7% oil blend (Clove oil:Menthol:Camphor, 94:10:10) |
| Carbopol 974P NF | 1 | 1 | 1 |
| Propylene Glycol | 15 | 15 | 15 |
| Poloxamer 407 | 9 | 9 | 9 |
| Polysorbate 20 | 5 | 5 | 6 |
| Sodium Saccharin | 0.2 | 0.2 | 0.2 |
| Sodium Benzoate | 0.2 | 0.2 | 0.2 |
| 50% NaOH Solution | 0.6 | 0.6 | 0.56 |
| Clove oil | — | — | 4.71 |
| Eugenol | — | 4 | — |
| Camphor | — | 0.5 | 0.5 |
| Menthol | 0.5 | 0.5 | 0.5 |
| Water | 68.5 | 64 | 62.33 |
| Total | 100 | 100 | 100 |

Example 2

Gels as described above are further optimized for providing soothing effect from cavity and sensitivity pain by optionally using small particle silica to provide rapid occlusion of dentinal tubules for sensitivity relief, and/or optionally using additional analgesic oils and/or potassium salt to provide additional pain relief. Additional polymer binders such as polyvinyl pyrolidone (Plasdone® S-630) or methyl vinyl ether/maleic anhydride copolymer (Gantrez®) provide additional matrix support to retain and control the release of the small particle silica or other actives and/or and herbal oils from the formulation. As in the previous example, the compositions are stabilised with emulsifiers and contain other excipients such as sweeteners, humectants and preservatives. These leave-on gel formulations are applied directly on the affected tooth surface or along the gum line to provide instant and long lasting relief from cavity and sensitivity related pain. As the process of preparing of a gel with herbal oils and occlusive agents is challenging, various combinations are tried to arrive at the most stable composition.

The following formulation prototypes are found to have good gel and delivery properties:

TABLE 8

Formulation prototype 1.5% Carbopol 974P NF gel and 5% Eugenol:Camphor:Menthol (80:10:10) with 5% KNO3 and 10% AC-43 Silica
1.0% Carbopol 974P NF gel and 5% Eugenol:Camphor:Menthol (80:10:10) with 10% AC-43 Silica
1.5% Carbopol 974P NF gel and 5% Eugenol:Camphor:Menthol (80:10:10), 10% AC-43 Silica binded by 2% Gantrez
1.5% Carbopol 974P NF gel and 5% Eugenol:Camphor:Menthol (80:10:10), 8% Arginine binded by 2% Gantrez
1.5% Carbopol 974P NF gel and 5% Eugenol:Camphor:Menthol (80:10:10), 10% AC-43 Silica binded by 2% Gantrez
1.5% Carbopol 974P NF gel and 5% Eugenol:Camphor:Menthol (80:10:10), 8% Arginine binded by 2% Gantrez
1.5% Carbopol 974P NF gel and 5%

TABLE 8-continued

Formulation prototype

Eugenol:Camphor:Menthol (80:10:10) + 0.5% astringents + 5% PVP
1.5% Carbopol 974P NF gel and 5% Eugenol:Camphor:Menthol (80:10:10) + 0.5% astringents + 5% PVP + 10% AC-43 Silica
1.5% Carbopol 974P NF gel and 5% Eugenol:Camphor:Menthol (80:10:10) + 0.5% astringents + 5% PVP + 0.5% Black Pepper oil + 0.5% Ginger oil The formulations are prepared according to the following scheme:
1. Disperse the Carbopol 974P NF in formula quantity of propylene glycol and some portion of water.
2. Ensure even dispersion and wetting of the Carbopol in propylene glycol and water blend with the help of homogenizer.
3. Avoid very high agitation to prevent air entrapment and lump formation.
4. Add formula quantity of Poloxamer 407, Polysorbate 20, sodium saccharin and sodium benzoate to the remaining amount of water.
5. Mix all the ingredients together at low speed in the mixer.
6. Continue mixing till an even dispersion is obtained.
7. After ensuring even dispersion of both blends, add the polymer dispersion to the poloxamer dispersion in the mixer.
8. Allow mixing of both till a smooth even dispersion is obtained.
9. Add formula quantity of oil blend to the dispersion and mix for some time without vacuum.
10. Then mix at high speed under full vacuum to ensure complete emusification
11. Add formula quantity of alkali to the dispersion at high speed and full vacuum to neutralize the polymer and to get the final thick gel Electrolytes like potassium nitrate, where present, are added in the propylene glycol-water blend before addition and dispersion of Carbopol. Where present, AC-43 Silica is added after the complete emulsification process. Additional inactive ingredients like thickening silica are added after addition of all other oils and actives but before the neutralization process. A detailed ingredient listing for some exemplary compositions of the present invention is provided below in Table 9.

TABLE 9

| | Formula option | | | | | |
|---|---|---|---|---|---|---|
| | OPTION-2 | OPTION-3 | OPTION-4 | OPTION-5 | OPTION-6 | OPTION-7 |
| | Description | | | | | |
| | Oil blend + anti-sensitivity + occlusive agent | Oil blend + occlusive agent | Oil blend + occlusive agent + binder | Oil blend + astringents + PVP | Oil blend + Thymol + astringents + film former + occlusive agent | Oil blend + astringents + film former + Black pepper oil + Ginger oil |
| Carbopol 974P NF | 1 | 1.5 | 1.5 | 1.5 | 1.5 | 1.5 |
| Propylene Glycol | 15 | 15 | 15 | 15 | 15 | 15 |
| Glycerin | — | — | — | — | — | — |
| Poloxamer 407 | 9 | 9 | 9 | 9 | 9 | 9 |
| Polysorbate 20 | 5 | 5 | 5 | 5 | 5 | 5 |
| Sodium Saccharin | 0.2 | 0.2 | 0.2 | 0.2 | 0.2 | 0.2 |
| Sodium Benzoate | 0.2 | 0.2 | 0.2 | 0.2 | 0.2 | 0.2 |
| 50% NaOH Solution | 0.8 | 0.8 | 1.5 | 0.8 | 1 | 1 |
| Clove oil | 4.9 | 4 | 4 | 4 | 4 | 4 |
| Camphor | 1.4 | 0.5 | 0.5 | 0.5 | 0.5 | 0.5 |
| Menthol | 0.7 | 0.5 | 0.5 | 0.5 | 0.5 | 0.5 |
| Potassium nitrate | 5 | — | — | — | — | — |
| AC-43 Silica | 10 | 10 | 10 | — | 10 | — |
| Thickening Silica | 8 | 8 | 8 | — | — | — |
| Thymol | — | — | — | 0.5 | 0.5 | 0.5 |
| *Terminalia chebula* extract (Dry Powder) | — | — | — | 0.5 | 0.5 | 0.5 |
| *Acacia catechu* extract (Dry Powder) | — | — | — | 0.5 | 0.5 | 0.5 |
| Ginger oil | — | — | — | — | — | 0.5 |
| Black Pepper oil | — | — | — | — | — | 0.5 |
| Gantrez | — | — | 2 | — | — | — |
| Plasdone S-630 | — | — | — | 5 | 5 | 5 |
| Water | 38.8 | 45.3 | 42.6 | 56.8 | 46.6 | 55.6 |
| Total | 100 | 100 | 100 | 100 | 100 | 100 |

Example 3

Gels as described above are further optimized for providing soothing effect from cavity and sensitivity by using arginine rather than sodium hydroxide to neutralize the polymer. The arginine provides a sustained and soothing buffering effect, and moreover is able to form complexes with available minerals in the oral cavity to plug the dentinal tubules, thereby reducing sensitivity. The arginine is added at the end of the formulation process, when it replaces the sodium hydroxide of the previous examples for purposes of neutralizing the anionic polymer and fixing the emulsion as a stable gel.

TABLE 10

| Description | Formula option OPTION-8 Oil blend + arginine |
| --- | --- |
| Carbopol 974P NF | 1.5 |
| Propylene Glycol | 15 |
| Glycerin | 6 |
| Poloxamer 407 | 9 |
| Polysorbate 20 | 5 |
| Sodium Saccharin | 0.2 |
| Sodium Benzoate | 0.2 |
| 50% NaOH Solution | — |
| Clove oil | 4 |
| Camphor | 0.5 |
| Menthol | 0.5 |
| Potassium nitrate | — |
| AC-43 Silica | — |
| Thickening Silica | — |
| Thymol | — |
| *Terminolia chebula* extract (Dry Powder) | — |
| *Acacia catechu* extract (Dry Powder) | — |
| Ginger oil | — |
| Black Pepper oil | — |
| Arginine | 8 |
| Gantrez | 2 |
| Plasdone S-630 | — |
| Water | 48.1 |
| Total | 100 |

We claim:

1. An orally acceptable topical analgesic gel comprising:
   a mixture of analgesic oils comprising (a) clove oil and/or eugenol, (b) a cooling agent, and (c) camphor; and
   an orally acceptable gel base comprising:
      an anionic polymer and a basic amino acid, wherein the gel base provides controlled release of the mixture of analgesic oils following application to a tooth, and wherein the ratio of (a) to (b) to (c) is 70-100:5-15:5-15.

2. The analgesic gel of claim 1, wherein the gel base releases an effective amount of the analgesic oils to the tooth after 30 seconds.

3. The analgesic gel of claim 1, wherein the gel base releases an effective amount of the analgesic oils to the tooth after 60 seconds.

4. The analgesic gel of claim 1, wherein the gel base delivers an effective amount of the analgesic oils to the tooth for at least 5 minutes.

5. The analgesic gel of claim 1, wherein the gel base delivers an effective amount of the analgesic oils to the tooth for up to 120 minutes.

6. The analgesic gel of claim 1, wherein the mixture of analgesic oils comprises 1-10% by weight of the formulation.

7. The analgesic gel of claim 1, wherein the cooling agent is menthol.

8. The analgesic gel of claim 1, wherein the ratio of (a) to (b) to (c) is from about 8:1:1 to about 10:1:1.

9. The analgesic gel of claim 1, wherein the mixture of analgesic oils comprises clove oil:menthol:camphor in a ratio of 8:1:1 to about 10:1:1.

10. The analgesic gel of claim 1, wherein the basic amino acid is selected from arginine, lysine, citrullene, ornithine, creatine, histidine, diaminobutanoic acid, diaminoproprionic acid.

11. The analgesic gel of claim 1, wherein the basic amino acid is arginine.

12. The analgesic gel of claim 1, wherein the basic amino acid is present in an amount sufficient to partially or fully neutralize the anionic polymer.

13. The analgesic gel of claim 1, wherein anionic polymer comprises a crosslinked poly(acrylic acid).

14. The analgesic gel of claim 1, wherein the gel base comprises a methyl vinyl ether/maleic anhydride (PVM/MA) copolymer.

15. The analgesic gel of claim 1, wherein the gel base comprises one or more nonionic surfactants selected from poloxamers, polysorbates, and mixtures thereof.

16. The analgesic gel of claim 1, wherein the gel base has pH about 6 to about 8.

17. The analgesic gel of claim 1, wherein the gel base comprises one or more astringents.

18. The analgesic gel of claim 1, wherein the gel base comprises a soluble potassium salt.

19. The analgesic gel of claim 1, wherein the gel base comprises a small particle occlusive agent.

20. The analgesic gel of claim 1, wherein the mixture of analgesic oils further comprises comprising a warming agent.

21. The gel of claim 1 wherein the gel base comprises:
   a. cross-linked poly(acrylic acid);
   b. propylene glycol;
   c. a nonionic surfactant selected from poloxamers, polysorbates, and mixtures thereof; and
   d. a neutralizing base.

22. The analgesic gel of claim 1, wherein the basic amino acid is present in an amount of from 4-12% by weight of the formulation.

* * * * *